(12) United States Patent
Crocker et al.

(10) Patent No.: US 7,094,326 B2
(45) Date of Patent: *Aug. 22, 2006

(54) ELECTRODES FOR MICROFLUIDIC APPLICATIONS

(75) Inventors: Robert W. Crocker, Fremont, CA (US); Cindy K. Harnett, Livermore, CA (US); Judith L. Rognlien, Livermore, CA (US)

(73) Assignee: Sandia National Laboratories, Livermore, CA (US)

( * ) Notice: Subject to any disclaimer, the term of this patent is extended or adjusted under 35 U.S.C. 154(b) by 505 days.

This patent is subject to a terminal disclaimer.

(21) Appl. No.: 10/330,607

(22) Filed: Dec. 24, 2002

(65) Prior Publication Data

US 2004/0118689 A1    Jun. 24, 2004

(51) Int. Cl.
*G01N 27/453* (2006.01)
*B28B 1/44* (2006.01)

(52) U.S. Cl. .................. 204/600; 204/280; 264/42
(58) Field of Classification Search ............... 204/600, 204/280, 432; 264/43, 42; 156/89.12, 89.14
See application file for complete search history.

(56) References Cited

U.S. PATENT DOCUMENTS

| | | | | |
|---|---|---|---|---|
| 3,843,400 A | * | 10/1974 | Radford et al. | ............. 429/152 |
| 5,556,580 A | * | 9/1996 | Suddith | ..................... 264/4.3 |
| 6,277,257 B1 | * | 8/2001 | Paul et al. | .................. 204/450 |
| 6,675,660 B1 | * | 1/2004 | Mosier et al. | ........... 73/861.07 |
| 6,890,409 B1 | * | 5/2005 | Woudenberg et al. | ...... 204/242 |

* cited by examiner

*Primary Examiner*—Kaj K. Olsen
(74) *Attorney, Agent, or Firm*—Donald A. Nissen

(57) ABSTRACT

An electrode device for high pressure applications. These electrodes, designed to withstand pressure of greater than 10,000 psi, are adapted for use in microfluidic devices that employ electrokinetic or electrophoretic flow. The electrode is composed, generally, of an outer electrically insulating tubular body having a porous ceramic frit material disposed in one end of the outer body. The pores of the porous ceramic material are filled with an ion conductive polymer resin. A conductive material situated on the upper surface of the porous ceramic frit material and, thus isolated from direct contact with the electrolyte, forms a gas diffusion electrode. A metal current collector, in contact with the gas diffusion electrode, provides connection to a voltage source.

16 Claims, 1 Drawing Sheet

US 7,094,326 B2

ELECTRODES FOR MICROFLUIDIC APPLICATIONS

STATEMENT OF GOVERNMENT INTEREST

This invention was made with Government support under contract no. DE-AC04-94AL85000 awarded by the U.S. Department of Energy to Sandia Corporation. The Government has certain rights in the invention.

CROSS-REFERENCE TO RELATED APPLICATIONS

Not applicable.

FIELD OF THE INVENTION

The present invention is directed to electrodes for applying electric fields and currents in high pressure systems and particularly for high pressure microfluidic systems.

BACKGROUND OF THE INVENTION

Electrodes are necessary elements in devices or applications that employ electric fields or currents to act on liquids. Microanalytical devices that employ electrophoresis, electroosmosis, electrokinetic pumping, and various electrochemical detection schemes pose demanding requirements for electrodes, in particular because these electrodes are required to function in miniaturized reservoirs and/or microchannels.

Electric fields and currents are employed in microseparation systems employing electrophoresis for separation and sample concentration. These include capillary electrophoresis (CE), capillary zone electrophoresis (CZE), capillary electrochromatography (CEC), micellar electrokinetic chromatography (MEKC), and electrokinetically-driven high pressure liquid chromatography (EK-HPLC).

Sample pre-concentration schemes employed prior to separation in microfluidic separation devices have been accomplished by a variety of means employing electric fields. Examples include sample stacking by electrophoresis across a region of non-uniform analyte mobility, isoelectric focusing employing electric fields along pH gradients, and electrophoretic concentration against an analyte impermeable barrier such as a salt bridge or solid-polymer electrolyte. Many miniaturized and conventional-scale analytical systems employ electrochemical detection of analyte species by measurement of the conductivity of the analyte fluid stream.

Moreover, in many of the applications discussed above pressures in excess of 1000 psi can be generated. By way of example, by applying voltage across a porous bed having a charged-solid-liquid interface, electrokinetic pumps are capable of developing pressures in excess of 10,000 psi.

All the applications described above require electrodes to provide the necessary electric fields and currents. The most common electrode in use is simply a metal wire, principally because of both the ease of insertion into the small dimensions of a microfluidic channel and sealing against high pressure. These wires are generally made of nickel, steel, platinum, gold, or other passive or noble metal. The disadvantage attached to the use of these metal wire electrodes in microscale devices, i.e., devices having fluid flow channels ≈ to 1000 µm, is the formation of gas bubbles, generally arising from the electrolysis of the solvent, e.g., water or formaldehyde. Because of the small dimensions of flow channels in microfluidic devices, these gas bubbles can occlude the current path to the electrodes and introduce electrical noise. In the worst case, the bubbles can block the entire flow channel and thereby open the electrical circuit. In flowing separation or detection systems, electrochemically produced hydrogen or oxygen can react with species of interest and bias or vitiate the analysis. Besides electrolytic gas bubble generation, electroactive species in the fluid being analyzed can be electrochemically reduced or oxidized on the exposed electrodes degrading the analysis and/or upsetting the separation or detection chemistry. In open or low-pressure systems and devices, conducting polymer or salt bridge devices have been used to separate electrodes away from sensitive areas in the device. However, in high pressure systems liquid permeation or loss of mechanical integrity precludes these conventional solutions. What is required is an electrode or electrode device that can be used in high pressure devices to provide the electric fields and currents necessary in the applications described above.

SUMMARY OF THE INVENTION

Accordingly, the present invention is directed generally to an electrode device for applying electric fields in high pressure microfluidic devices without the disadvantage of generating gas bubbles that can block microchannels or introduce electrical noise.

In one embodiment the electrode device comprises:
 a tubular duct having electrically insulating or otherwise non-electrically conducting walls in fluid communication with a fluid channel;
 a frit having an upper and a lower surface disposed in one end of said tubular duct, wherein the lower surface of said frit is exposed to the fluid channel, and wherein the pores of the porous rigid dielectric material are filled with an ion conductive polymer material;
 a gas diffusion electrode disposed on the upper surface of the frit; and
 a metal current collector in contact with the gas diffusion electrode.

DETAILED DESCRIPTION OF THE INVENTION

Figure 1:
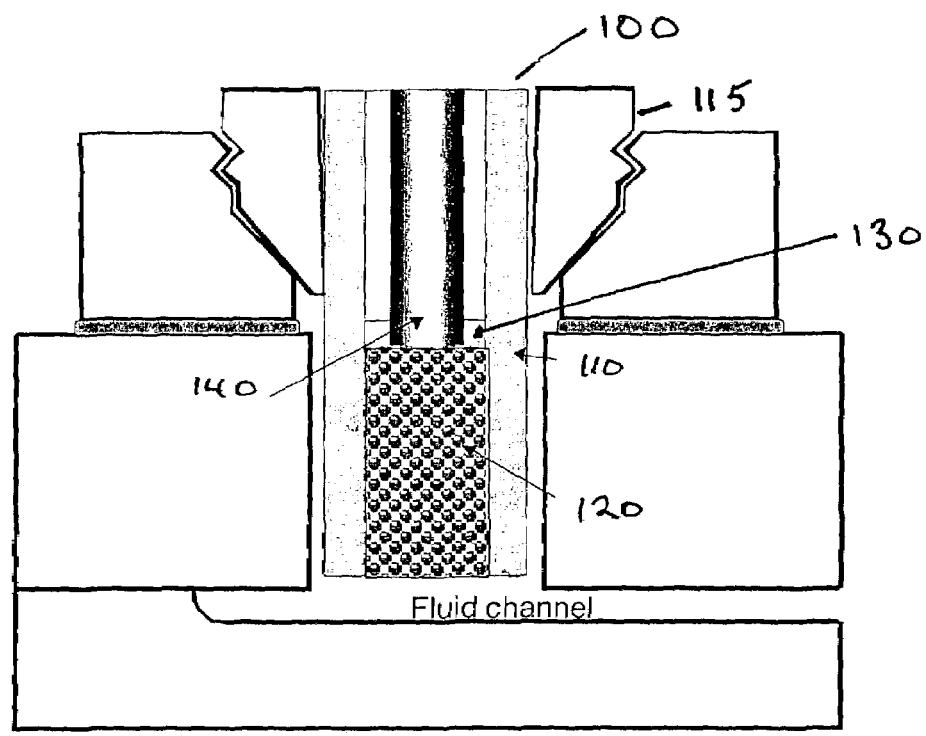
FIG. 1 is shows a schematic illustration of the invention.

FIG. 1 is a cross-section of high pressure gas diffusion device 100 that embodies the invention and illustrates and exemplifies the invention. In this embodiment a tubular duct, in this instance, a glass capillary tube 110 is retained and positioned in a fluid channel by a high pressure fitting 115. The capillary and associated fitting form an electrically non-conductive passageway to a microfluidic channel that can be at high pressure. High pressure is defined as a pressure in excess of about 50 psi. A porous, rigid, dielectric monolithic frit 120 is formed in the end of the capillary tube. One mode of forming the frit can be to insert one end of the capillary tube into a slurry consisting of ceramic beads in a size range of from about 5 to 50 µm. The choice of the size of the ceramic beads is a balance between a frit pore size (void space) being too small to allow a subsequently added polymer ionomer resin to flow through the frit (<5 µm) and too large (>50 µm) such that the frit does not possess sufficient structural strength to withstand high pressure intrusion of the polymer ionomer resin into the frit structure.

Almost any rigid non-conducting ceramic bead material such as silica, alumina, or titania can be used to form the structure of the frit, and monodisperse beads are preferred from a permeability and strength perspective. In order to form a frit structure that can withstand high pressures the individual ceramic beads have to be bonded together and the frit structure bonded to the capillary wall by a method that preserves the porosity of the structure. This can be either by thermal fusion or, preferably, by adhesive bonding. Adhesives such as sodium silicate and other sol-gel alcohol precursors solutions such as aluminum butoxide, tetramethyl and tetraethyl orthosilicate, titanium tetra(isopropoxide), and zirconium tetrapropoxide could be used.

After the frit structure has been formed, the pores of frit 120 are filled with an ion conductive material such as a polymer ionomer resin. The composition of the frit material as well as the ion conductive material are determined generally by the function of the electrode, i.e., whether it is designed to act as an anode or a cathode, and the pH of the fluid. In the case where the electrode acts as a cathode the ion conductive material can be a cation selective polymer material such as Nafion™ (a perfluorosulfonic acid/PTFE copolymer sold by DuPont). Anion selective and non-selective solid polymer electrolyte materials are also available depending on the specific application. Examples of these materials can be found in U.S. patent application Ser. No. 09/796,762, "Castable Three-dimensional Stationary Phase for Electric Field-driven Applications" incorporated herein by reference in its entirety. A gas diffusion electrode 130 is formed on the upper surface of frit 120 by disposing a mixture of the ion conductive material and a material that is an electronic conductor, such as a metal or carbon foam or metal or carbon fiber mat, thereon. A conductive carbon or metal powder can also be used such as a platinum, gold, silver, platinum, palladium powder. A metal current collector 140 contacts gas diffusion electrode 130 to an external power supply (not shown). The metal current collector can be nickel, steel, palladium, platinum, gold, or other passive or noble metal.

In operation, an electric potential that can be at high voltage is applied to the current collector 140 of the electrode device from a power supply. Electric current flows between the power supply and the electrode device, the direction depending on the electric potential relative to the fluid in the channel. The anodic or cathodic potential difference between the gas diffusion electrode 130 and the fluid in the channel drives electrochemical oxidation or reduction, respectively, of labile solvent or solute species such as water at the gas diffusion electrode. Gaseous products of the electrochemical reaction diffuse out of the gas diffusion electrode and up the glass capillary to the exterior of the electrode device, thus preventing the accumulation of dissolved gasses and subsequent deleterious formation of bubbles in the fluidic channel.

The depletion of the reactive species at the gas diffusion electrode/ionomer-frit composite interface drives a diffusion flux from the channel to replenish the reactant. Ionic species from the electrode reaction are either driven through the ionomer composite 120 into the fluid in the channel as would be the case for hydrogen ions from the anodic oxidation of water; or are neutralized by ionic species of the opposite charge migrating in from the fluid in the channel driven by the electric field, for example hydrogen cations from an acidic aqueous fluid in the channel to combine with hydroxyl anions from the reduction of water at the electrode.

Other electrochemically reactive species besides water are effective in the electrode function. The selection of ionomer for the composite component should be made based on its permeability of the neutral and ionic species to facilitate the desired electrochemical reaction. For example, the cationic selective Nafion™ ionomer is most suitable for acidic aqueous fluids, and reasonably effective for neutral and basic solutions as well. Zwitterion ionomers such as those described in U.S. patent application Ser. No. 10/253,144 "Method for Improving the Performance of Electrokinetic Pumps" incorporated herein by reference in its entirety, may also be generally used.

As an anode in an electrochemical circuit, the electrode device provides the positive potential for the applied electric field. Electric current from the power supply, which can be supplied at high voltage, flows into gas diffusion electrode 130 through current collector wire 140. The potential difference between the power supply and the fluid contacting the gas diffusion electrode drives the electrochemical oxidation of water at the gas diffusion electrode/current collector interface. In response to the depletion of water by electrochemical oxidation at the gas diffusion electrode, a concentration gradient is produced across the ionomer/frit interface that drives a diffusion flux to replenish the water at the gas diffusion electrode.

The cathodic operation of the electrode device is different. Here, electric current is drawn from gas diffusion electrode 130 through current collector wire 140 to the power supply by the application of a potential more negative that that in the fluid channel. The potential difference between the power supply and the gas diffusion electrode drives the electrochemical reduction of hydrogen ions within the gas diffusion electrode. The product of that reaction, hydrogen gas, can be vented through an external opening in the capillary tube. The electric field gradient across the cation-selective ionomer/frit composite drives an ionic current of hydrogen ions through the ionomer to supply the gas diffusion electrode. Other less mobile cations can migrate through the ionomer in minor amounts to form their hydroxides on the gas diffusion electrode.

In order to understand the invention better, an example of electrode fabrication is given below. This example is merely illustrative of an embodiment of this invention and many other embodiments and modifications can be made by those of skill in the art without departing from the spirit and scope of the invention as defined in the claims.

EXAMPLE

1. A tubular duct comprising a length of 100 μm ID glass capillary tubing, about 2–3cm in length, was cut from a piece of commercial glass capillary tubing. It is preferred that cutting be with a fiber optic cutting tool in order to produce a square end.
2. 5 μm diameter porous silica beads (Nucleosil™, Macherey-Nagel and Co.), wetted with a sodium silicate/water solution (2:3), were introduced into one end of the capillary tubing to form a porous frit and the frit was dried. A preferred procedure is to dry the frit at about 40° C. for about 12 hrs using purely electric or laser thermal methods.
3. A quantity of a solution of 20% Nafion in a solvent such as an alcohol or a perfluorinated liquid was introduced into the unfritted end of the glass capillary.
4. Subsequently, a slurry comprising 1 μm Pd powder and the Nafion solution was injected into the unfritted end of the capillary. It is preferred that the ratio of Pd powder to Nafion be such that when the slurry dries the Pd is present at a concentration of about 10 wt %.

5. The Nafion/alcohol/Pd powder slurry was forced into the interstices of the silica frit. Forcing can be by air pressure.

6. The Nafion/alcohol solution was air-dried for about 6–10 hours at which time a metal wire current collector was inserted into the Pd metal gas diffusion electrode. The metal wire can be stainless steel, a noble metal such as Pt, Pd, or Au, or a Ni/Cr alloy.

7. The electrode device was dried at a temperature of about 80° C. for about 1 hour.

Figure 2:
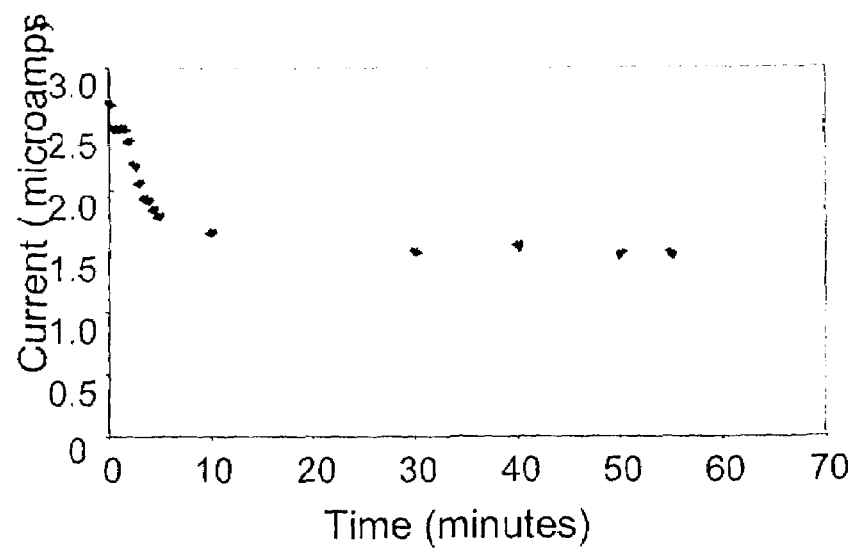
FIG. 2 shows the electrical response of the electrode device.

Electrodes fabricated in the manner described above have been found to withstand pressures of greater than 10,000 psi without visible damage or leaks. The impedance of these electrode devices was between about 0.2 to $5 \times 10^6$ ohm. An example of the performance of the electrode device at an applied potential of 5 V is given in FIG. 2.

We claim:

1. An electrode device for use in high pressure microfluidic applications, comprising:
    a tubular duct having electrically insulating or otherwise non-electrically conducting walls in fluid communication with a fluid channel;
    a frit having an upper and a lower surface disposed in one end of said tubular duct, wherein the lower surface of said frit is exposed to the fluid channel, and wherein the pores of the frit material are filled with an ion conductive polymer material;
    a gas diffusion electrode disposed on the upper surface of the frit; and
    a metal current collector in contact with the gas diffusion electrode.

2. The electrode of claim 1, wherein said tubular duct comprises a capillary tube.

3. The electrode of claim 1, wherein the fluid channel is at high pressure.

4. The electrode of claim 1, wherein said frit comprises a porous rigid dielectric material.

5. The electrode of claim 4, wherein the porous rigid dielectric material comprises ceramic beads.

6. The electrode of claim 5, wherein the ceramic beads have a diameter in the range of 5 to 50 µm.

7. The electrode of claim 6, wherein the ceramic beads are silica beads, alumina beads, or titania beads.

8. The electrode of claim 1, wherein said gas diffusion electrode comprises a mixture of an ion conductive polymer and an electronically conductive material.

9. The electrode of claim 8, wherein the electronically conductive material is a metal foam, a metal powder, a metal fiber mat, or a carbon fiber mat.

10. The electrode of claim 9, wherein the metal powder is platinum, gold, silver, platinum, or palladium.

11. The electrode of claim 1, wherein the ion conductive polymer material includes a cation-selective perfluorosulfonate ionomer.

12. A method for making an electrode for high pressure microfluidic applications, comprising:
    providing a tubular duct material;
    inserting a quantity of ceramic beads into one end of the tubular duct;
    bonding the ceramic beads together to form a porous frit and simultaneously bonding the frit to the wall of the tubular duct;
    injecting an ion conductive polymer into the pores of the frit;
    disposing a gas diffusion electrode onto the upper surface of the frit; and
    contacting the gas diffusion electrode with a metal current collector.

13. The method of claim 12, wherein said step of bonding includes thermal fusion or adhesive bonding.

14. The method of claim 13, wherein adhesive bonding is by contacting the ceramic beads and duct wall with a solution of an adhesive material.

15. The method of claim 14, wherein the adhesive material include sodium silicate or sol-gel alcohol precursors.

16. The method of claim 15, wherein the sol-gel precursors are selected from a group including aluminum butoxide, tetramethyl, tetraethyl orthosilicate, titanium tetra(isopropoxide), or zirconium tetrapropoxide.

* * * * *